United States Patent
Yagi et al.

(10) Patent No.: US 10,605,437 B2
(45) Date of Patent: Mar. 31, 2020

(54) LIGHT PROJECTING DEVICE

(71) Applicant: CCS Inc., Kyoto-shi, Kyoto (JP)

(72) Inventors: Motonao Yagi, Kyoto (JP); Atsushi Miyatake, Kyoto (JP)

(73) Assignee: CCS INC., Kyoto-Shi, Tokyo (JP)

( * ) Notice: Subject to any disclaimer, the term of this patent is extended or adjusted under 35 U.S.C. 154(b) by 0 days.

(21) Appl. No.: 15/742,855

(22) PCT Filed: Jun. 22, 2016

(86) PCT No.: PCT/JP2016/068467
§ 371 (c)(1),
(2) Date: Jan. 8, 2018

(87) PCT Pub. No.: WO2017/018101
PCT Pub. Date: Feb. 2, 2017

(65) Prior Publication Data
US 2018/0202633 A1 Jul. 19, 2018

(30) Foreign Application Priority Data

Jul. 29, 2015 (JP) .................................. 2015-149206

(51) Int. Cl.
*F21V 17/02* (2006.01)
*H04N 1/028* (2006.01)
(Continued)

(52) U.S. Cl.
CPC ................ *F21V 17/02* (2013.01); *F21V 3/02* (2013.01); *F21V 7/04* (2013.01); *F21V 29/76* (2015.01);
(Continued)

(58) Field of Classification Search
CPC . F21V 17/02; F21V 29/76; F21V 3/02; F21V 7/04; G01N 21/474; G01N 21/8806; H04N 1/02815
(Continued)

(56) References Cited

U.S. PATENT DOCUMENTS 5,440,127 A * 8/1995 Squyres ................ B07C 5/3422
250/341.8
5,638,961 A * 6/1997 Satake ................... B07C 5/3425
209/580
(Continued)

FOREIGN PATENT DOCUMENTS

| CN | 101493423 A | 7/2009 |
|----|-------------|--------|
| CN | 101676769 A | 3/2010 |

(Continued)

OTHER PUBLICATIONS

ISA Japan Patent Office, International Search Report Issued in PCT Application No. PCT/JP2016/068467, dated Sep. 13, 2016, WIPO, 4 pages. (Submitted with English Translation of International Search Report).

(Continued)

*Primary Examiner* — Bryon T Gyllstrom
(74) *Attorney, Agent, or Firm* — Alleman Hall Creasman & Tuttle LLP

(57) ABSTRACT

In order to make it possible to image the surface of a workpiece from a plurality of directions without reducing the amount of light to be projected to the workpiece, a light projection device having light emitting surfaces opposite to the workpiece and formed with a slit allowing light reflected by the workpiece to pass from the light emitting surface side toward an opposite side thereof is adapted such that the slit (Continued)

is formed in a tapered shape whose width gradually increases from the light emitting surface side toward the opposite side.

8 Claims, 8 Drawing Sheets

(51) Int. Cl.
    *G01N 21/47*     (2006.01)
    *F21V 29/76*     (2015.01)
    *F21V 3/02*     (2006.01)
    *F21V 7/04*     (2006.01)
    *G01N 21/88*     (2006.01)
    *G01N 21/86*     (2006.01)
    *G01N 21/89*     (2006.01)
    *F21Y 115/10*     (2016.01)
    *H04N 5/225*     (2006.01)

(52) U.S. Cl.
    CPC ....... *G01N 21/474* (2013.01); *G01N 21/8806* (2013.01); *H04N 1/0288* (2013.01); *F21Y 2115/10* (2016.08); *G01N 21/86* (2013.01); *G01N 21/8901* (2013.01); *G01N 2021/8816* (2013.01); *G01N 2201/062* (2013.01); *H04N 5/2256* (2013.01)

(58) Field of Classification Search
    USPC ........................................................ 362/235
    See application file for complete search history.

(56) References Cited

U.S. PATENT DOCUMENTS

| | | | | |
|---|---|---|---|---|
| 5,884,775 A | * | 3/1999 | Campbell | B07C 5/3422 209/581 |
| 6,286,655 B1 | * | 9/2001 | Grubbs | B03B 9/061 198/462.1 |
| 6,369,882 B1 | * | 4/2002 | Bruner | B07C 5/342 209/577 |
| 6,424,416 B1 | * | 7/2002 | Gross | G01J 3/02 356/326 |
| 6,450,664 B1 | * | 9/2002 | Kelly | F21V 5/045 362/244 |
| 7,019,822 B1 | * | 3/2006 | Doak | B07C 5/342 356/73 |
| 2003/0095260 A1 | * | 5/2003 | Yoneda | G01N 21/8806 356/446 |
| 2008/0316483 A1 | * | 12/2008 | Tai | G01N 21/35 356/326 |
| 2015/0116791 A1 | * | 4/2015 | Tochigi | H04N 1/1039 358/475 |

FOREIGN PATENT DOCUMENTS

| | | |
|---|---|---|
| EP | 1950554 A1 | 7/2008 |
| JP | 2004022327 A | 1/2004 |
| JP | 2004144565 A | 5/2004 |
| JP | 2005214877 A | 8/2005 |
| JP | 2008102103 A | 5/2008 |
| JP | 2010112786 A | 5/2010 |
| JP | 2011069651 A | 4/2011 |
| WO | 9716024 A1 | 5/1997 |
| WO | 2013099981 A1 | 7/2013 |

OTHER PUBLICATIONS

European Patent Office, Extended European Search Report Issued in Application No. 16 830 206.5, dated Mar. 19, 2019, Germany, 7 pages.

China National Intellectual Property Administration, Office Action and Search Report Issued in Application No. 201680044022.5, dated Nov. 6, 2019, 7 pages.

* cited by examiner

LIGHT PROJECTING DEVICE

TECHNICAL FIELD

The present invention relates to a light projection device used to project light to a workpiece such as a product to make inspections, such as to check whether or not any flaws exist and to read a mark.

BACKGROUND ART

As this sort of light projection device, as disclosed in Patent Literature 1, there is one configured to be arranged between a workpiece and an imaging device for imaging the workpiece and project light from a light emitting surface facing the workpiece.

More specifically, this one includes a light emitting plate having the light emitting surface, and is configured such that, by forming a plurality of slits in the light emitting plate, the imaging device can image the surface of the workpiece from different directions through the slits.

However, in the above-described configuration, the plurality of slits are formed in the light emitting plate, and therefore as compared with a configuration adapted to form a single slit, the area of the light emitting surface is decreased to reduce the light amount of light to be projected to the workpiece, causing the problems of reducing inspection accuracy and inspection speed.

CITATION LIST

Patent Literature

Patent Literature 1
Japanese Unexamined Patent Publication JP-A2011-69651

SUMMARY OF INVENTION

Technical Problem

Therefore, the present invention is made in order to solve the above-described issues, and a main object thereof is to provide a light projection device capable of imaging the surface of a workpiece from a plurality of directions without reducing the amount of light to be projected to the workpiece.

Solution to Problem

That is, the light projection device according to the present invention is a light projection device including a light emitting surface facing a workpiece and formed with a slit allowing light reflected by the workpiece to pass from a light emitting surface side to an opposite side thereof, and characterized in that the slit has a shape whose width gradually increases from the light emitting surface side toward the opposite side.

In such a light projection device, since the slit allowing the light reflected by the workpiece to pass from the light emitting surface side toward the side opposite to it has the shape whose width gradually widens from the light emitting surface side toward the side opposite to it, a reduction in the light emitting surface due to the formation of the slit can be suppressed as much as possible, and a direction to image the surface of the workpiece can be changed depending on widening of the slit without reducing the amount of light to be projected to the workpiece.

In doing so, for example, depending on the roughness state of the surface of the workpiece, the type of a flaw, or the like, by making the imaging device directly face the workpiece, an image can be taken with the specular reflection component of the light reflected by the surface of the workpiece removed, or by tilting the imaging device, an image can be taken using the specular reflection component.

Note that the shape of the slit may be any shape as long as the shape is such that an opening width on the light emitting surface side is gradually made narrower than an opening width on the opposite side, and as one example, a tapered shape spreading toward the side opposite to the light emitting surface side can be cited.

As a specific embodiment of the light emitting surface, a flat surface can be cited, and in the case of a flat surface, the light emitting surface can be brought close to the workpiece, and the illuminance of light to be projected to the workpiece can be increased.

In order to increase the light amount of light to be projected to the light emitting surface, it is preferable to further include a plurality of LED light sources provided on a side opposite to the workpiece with respect to the light emitting surface.

As a specific embodiment for forming the above-described slit, a configuration adapted to further include: a light emitting plate formed with the light emitting surface; and a pair of casings that have openings closed by the light emitting plate, contain a plurality of LED light sources provided opposite to the openings, and are provided opposite to each other, in which opposite surfaces of the pair of casings, which are opposite to each other, form the slit can be cited.

Also, in order to emit uniform light from the light emitting surface, the following configurations are preferable.

A configuration is such that the openings are of a substantially rectangular shape, among side walls of the casings, which form the openings, inner surfaces of side walls on slit sides and inner surfaces of side walls on counter slit sides are provided with reflective members adapted to reflect light from the LED light sources toward the openings, and reflective members on the slit sides are larger in area of a reflective surface than reflective members on the counter slit sides.

A configuration is such that the plurality of LED light sources are provided sandwiching the slit on both sides thereof, and arranged more densely toward the slit sides than toward the counter slit sides.

A configuration is such that LED boards that are provided sandwiching the slit, on both sides thereof, and opposite to the light emitting plate, and mounted with the plurality of LED light sources are further included, and the LED boards are arranged tilted such that the slit sides are farther from the light emitting plate than the counter slit sides.

In these configurations, light from the LED light sources is thoroughly uniformly spread from the slit sides to counter slit sides of the light emitting plate, thus making it possible to, for example, prevent part of the slit sides of the light emitting plates from darkening as compared with the other parts.

Also, it is preferable that bottom walls of the casings, which are opposite to the light emitting plate, are tilted such that the slit sides are farther from the light emitting plate than the counter slit sides, and inner surfaces of the bottom walls are provided with the LED boards while outer surfaces of the bottom walls are provided with heat radiating members.

In such a configuration, since the bottom walls are tilted such that the slit sides are farther from the light emitting plate than the counter slit sides, the heat radiating members can be arranged so as to avoid overlap with the slit, and the heat radiating members can be prevented from blocking light.

In order to make it possible to change an imageable area, it is preferable that a connecting member connecting the pair of casings is further included, and the connecting member includes a slit width changing mechanism adapted to change the separation distance between the pair of casings and change the width of the slit.

Advantageous Effects of Invention

According to the present invention configured as described above, the surface of a workpiece can be imaged from a plurality of directions without reducing the amount of light to be projected to the workpiece.

LIST OF REFERENCE CHARACTERS

100 Light projection device
S Slit
10 Light emitting plate
11 Light emitting surface
14 Light emitting plate element
20 Casing
21 Opening
25 Opposite surface
32 LED light source
C Imaging device
W Workpiece

DESCRIPTION OF EMBODIMENTS

In the following, one embodiment of the light projection device according to the present invention will be described with reference to drawings.

Figure 1:
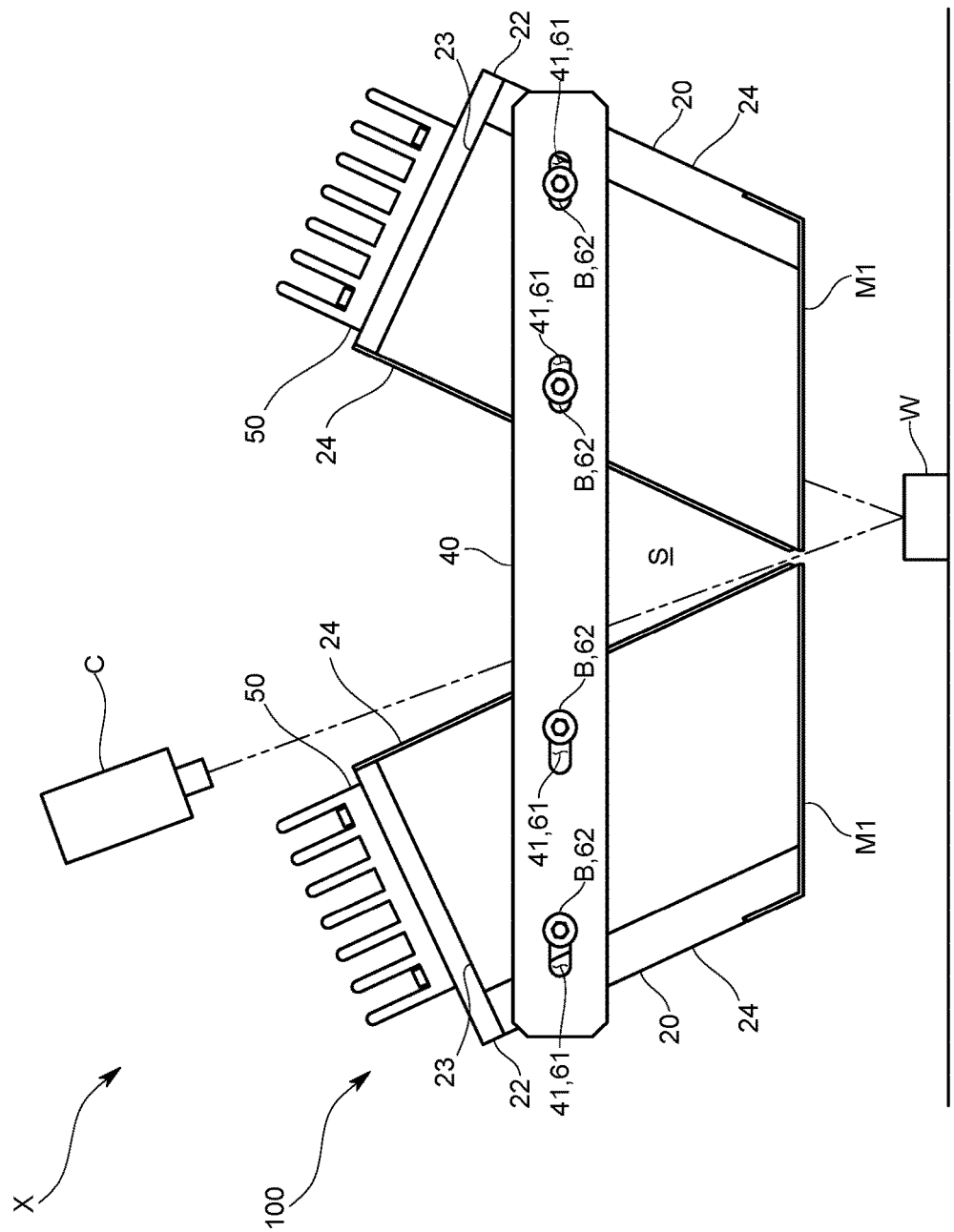
FIG. 1 is a side view illustrating the configuration of a light projection device in the present embodiment.

A light projection device 100 according to the present embodiment, as illustrated in FIG. 1, projects light to a workpiece W (an inspection object), and is used for, for example, a product inspection system X or the like adapted to image a predetermined area of the workpiece W by an imaging device C called a line sensor camera, and take the resulting image data into an image processor (not illustrated) to make a surface inspection whether or not there is any flaw or the like.

In addition, the workpiece W in the present embodiment is, for example, a continuous object flowing in a predetermined direction at a constant speed, such as paper or film, or an individual article placed on a conveyor and continuously conveyed, such as a cut film or a cut glass.

Figure 2:
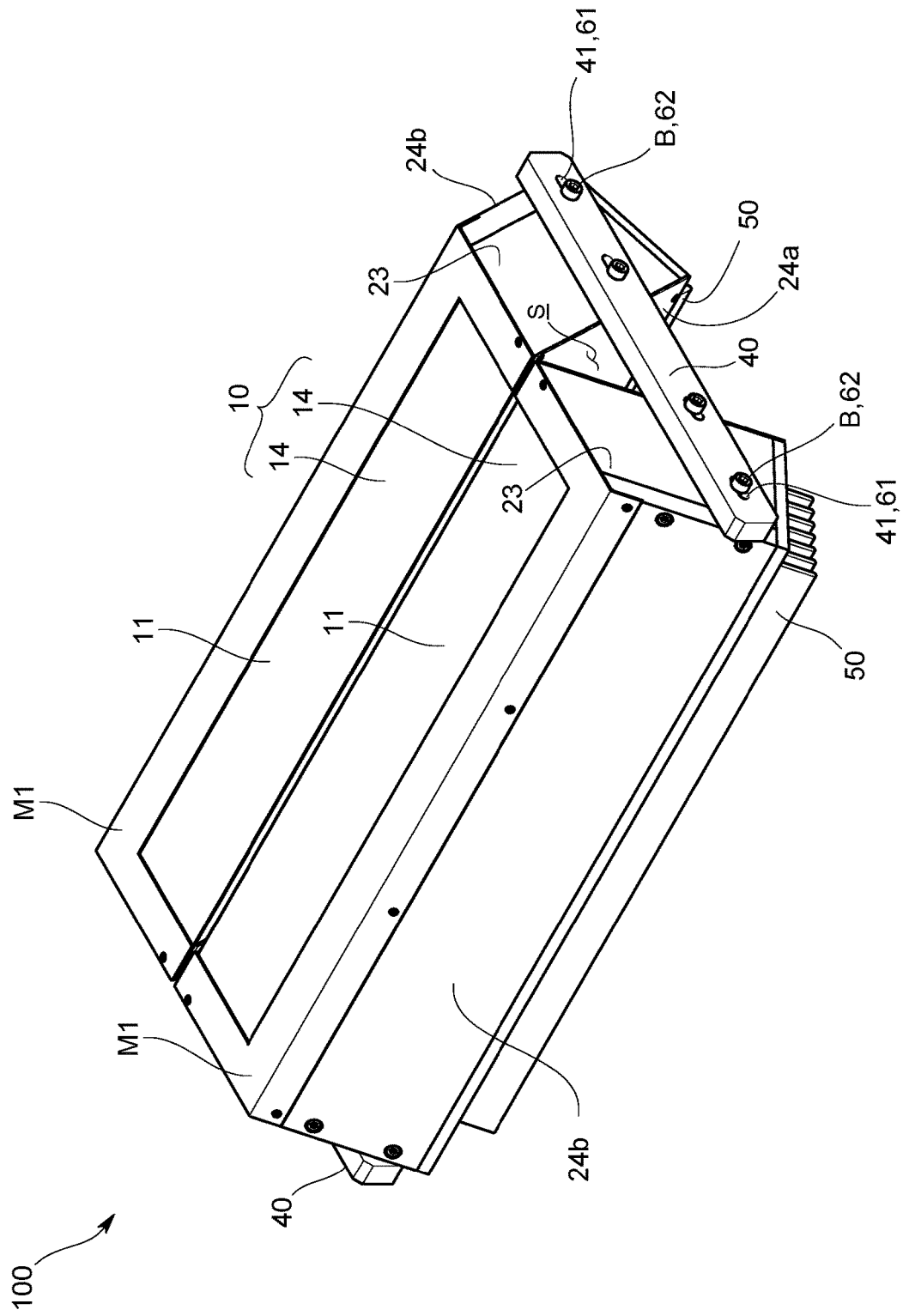
FIG. 2 is a perspective view illustrating the configuration of the light projection device in the same embodiment.
Figure 3:
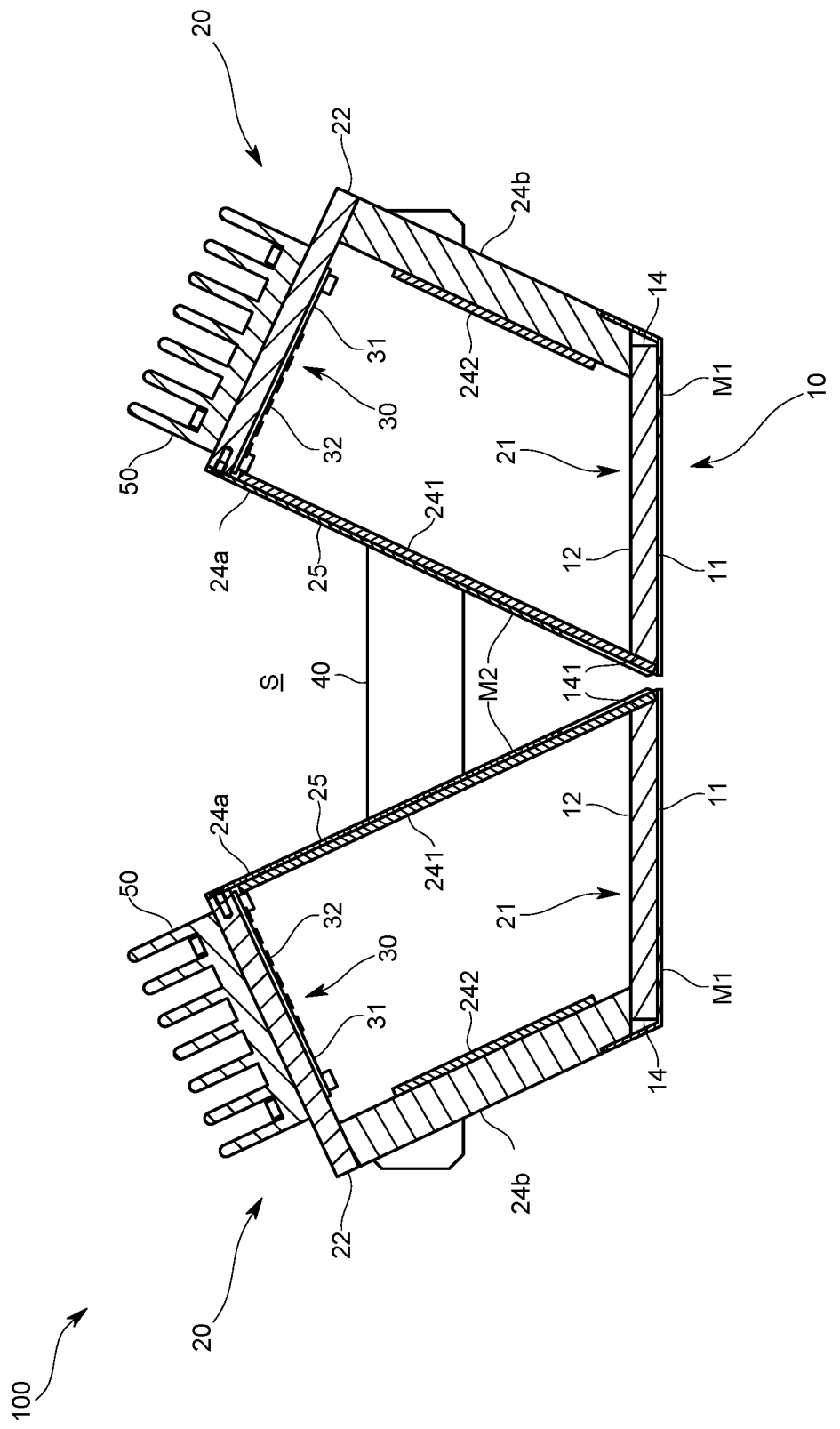
FIG. 3 is a cross-sectional view illustrating the configuration of the light projection device in the same embodiment.

The light projection device 100 is one arranged between the workpiece W and the imaging device C, and specifically, as illustrated in FIG. 1 to FIG. 3, includes: a light emitting plate 10 having light emitting surfaces 11 facing the workpiece W; casings 20 having openings 21 closed by the light emitting plate 10; and light source units 30 contained in the casings 20.

As illustrated in FIG. 1 to FIG. 3, the light emitting plate 10 has back surfaces 12 (surfaces on the sides opposite to the light emitting surfaces 11) to which light from the below-described light source units 30 is projected and that emits light from the light emitting surfaces 11 toward the workpiece W.

The light emitting plate 10 in the present embodiment is a translucent diffuser plate of, for example, a rectangular flat plate shape, whose light emitting surfaces 11 are flat surfaces, and formed of a pair of light emitting plate elements 14.

The respective light emitting elements 14 are arranged in the same plane separately from each other as particularly illustrated in FIG. 3, and between them, form a space allowing part of light reflected by the workpiece W to pass from the light emitting surfaces 11 side toward the opposite side, and have the same shape as each other here. In the present embodiment, one side surfaces 141 of the respective light emitting plate elements 14 are tilted so as to make the areas of the light emitting surfaces 11 larger than the areas of the back surfaces 12, and the respective light emitting plate elements 14 are arranged such that the one side surfaces 141 are opposite to each other.

As illustrated in FIG. 1 to FIG. 3, the casings 20 have the openings 21 closed by the light emitting plate 10, and the light emitting plate 10 is arranged facing the workpiece W. In the present embodiment, the casings 20 that are long-shaped and paired are mutually separately installed together, and an opening 21 of one of the casings 20 is provided with one of the light emitting plate elements 14, whereas an opening 21 of the other casing 20 is provided with the other light emitting plate element 14.

In addition, the outer peripheral parts of the light emitting surfaces 11 of the respective light emitting plate elements 14 are provided with metal plates M1 for fixing the respective light emitting plate elements 14 to the casings 20.

The above-described configuration forms, between the pair of casings 20, a slit S allowing the light reflected by the workpiece W to pass from the light emitting surfaces 11 side toward the opposite side thereof, and through the slit S, the imaging device C can image a predetermined area of the workpiece W.

More specifically, the respective casings 20 have substantially rectangular-shaped bottom walls 22 extending in the longitudinal direction, side walls provided on both ends of the bottom walls 22 in the longitudinal direction (hereinafter also referred to as short side walls 23), side walls provided on both ends of the bottom walls 22 in the width direction (hereinafter also referred to as long side walls 24), and the openings 21 of a substantially rectangular shape are formed opposite to the bottom walls 22 by the respective side walls 23, 24.

The bottom walls 22 are provided on the inner surfaces thereof with the below-described light source unit 30 as well as attached on the outer surfaces thereof with heat radiating members 50 such as heat sinks with, for example, screws or the like, and in the present embodiment, tilted such that the slit S sides are farther from the light emitting plate elements 14 than the counter slit sides.

Among the short side walls 23, a short side wall 23 provided at one end side of one of the casings 20 in the longitudinal direction, and a short side wall 23 provided at the one end side of the other casing 20 in the longitudinal direction are fixed and connected by a common connecting member 40. Also, a short side wall 23 provided at the other end side of the one casing 20 in the longitudinal direction and a short side wall 23 provided at the other end side of the other casing 20 in the longitudinal direction are fixed and connected by a common connecting member 40.

The connecting members 40 are, for example, flat plate-shaped, and have multiple through-holes 41 formed penetrating in the thickness direction, and the short side walls 23 are fixed by fasteners B inserted into the through-holes 41, such as bolts.

Among the long side walls 24, the long side walls 24 on the slit S sides (hereinafter also referred to as slit-side side walls 24a) are opposite to each other as particularly illustrated in FIG. 3, and between them, the slit S of a tapered shape whose width gradually increases from the light emitting surfaces 11 side toward the opposite side is formed.

More specifically, the respective slit-side side walls 24a are tilted so as to gradually increase a separation distance from the workpiece W side toward the imaging device C side, and this allows opposite surfaces 25 of the pair of casings 20 to spread the opening therebetween from the light emitting surfaces 11 side toward the opposite side.

Here, the spread angle between the opposite surfaces 25 is set to be substantially the same as the spread angle between the above-described one side surfaces 141 of the pair of the light emitting plate elements 14, and an imaging direction of the imaging device C is adapted to be changeable within the range of the spread angle.

Specifically, the slit-side side walls 24a in the present embodiment are configured to include reflective members 241 (hereinafter also referred to as first reflective plates 241) and metal plates M2 for fixing the first reflective plates 241 to the casings 20, and the metal plates M2 are screwed to the bottom walls 22.

Among the long side walls 24, long side walls 24 (hereinafter also referred to as counter slit-side side walls 24b) on the side opposite to the slit-side side walls 24a are provided parallel to the slit-side side walls 24a, and on the inner surfaces thereof, reflective members 242 (hereinafter also referred to as second reflective plates 242) are provided. The second reflective plates 242 are provided so as to cover parts of the inner surfaces of the counter slit-side side walls 24b and smaller in area than the first reflective plates 241.

The light source units 30 are adapted to project light to the back surfaces 12 of the light emitting plate 10, and as illustrated in FIG. 3, contained in the above-described respective casings 20 as well as provided on the side opposite to the workpiece W with respect to the light emitting surfaces 11.

In addition, the respective light source units 30 are adapted to be dimming-controlled on the basis of control signals transmitted from an unillustrated control part, such as ON/OFF signals or light amount signals, and here configured to be independently controllable.

Specifically, the respective light source units 30 include LED boards 31 provided opposite to the light emitting plate elements 14 and a plurality of LED light sources 32 mounted on the LED boards 31.

The LED boards 31 are, for example, screwed to the bottom walls 22, and in doing so, as with the bottom walls 22, tilted such that the slit S sides are farther from the light emitting plate elements 14 than the counter slit sides.

The large numbers of LED light sources 32 are laid along the longitudinal direction and width direction of the LED boards 31, and here arranged on the slit S sides more densely than on the counter slit sides.

Note that as a specific embodiment for the dense arrangement, for example, an embodiment adapted to make a separation distance between adjacent LED light sources 32 provided on the slit S sides along the width direction shorter than on the counter slit sides, an embodiment adapted to bring the plurality of LED light sources 32 arrayed at regular intervals close to the slit S sides of the LED boards 31 totally, or the like can be cited.

Further, the light projection device 100 of the present embodiment includes a slit width changing mechanism 60 adapted to change the width size of the above-described slit S.

Specifically, the slit width changing mechanism 60 is configured to include: slide grooves 61 that are formed in one set of the above-described short side walls 23 and the connecting members 40 and extend along the width direction of the slit S; and sliding bodies 62 that are fixed to the other set of the short side walls 23 and the connecting members 40, and slide in the slide grooves 61.

Figure 4A:
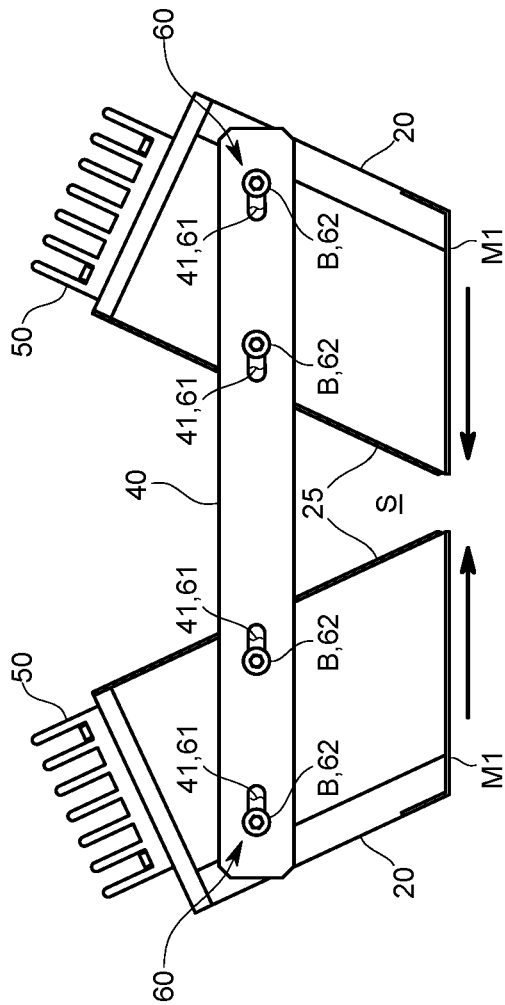
FIGS. 4A and 4B are schematic views illustrating the configuration of a slit width changing mechanism in the same embodiment.
Figure 4B:
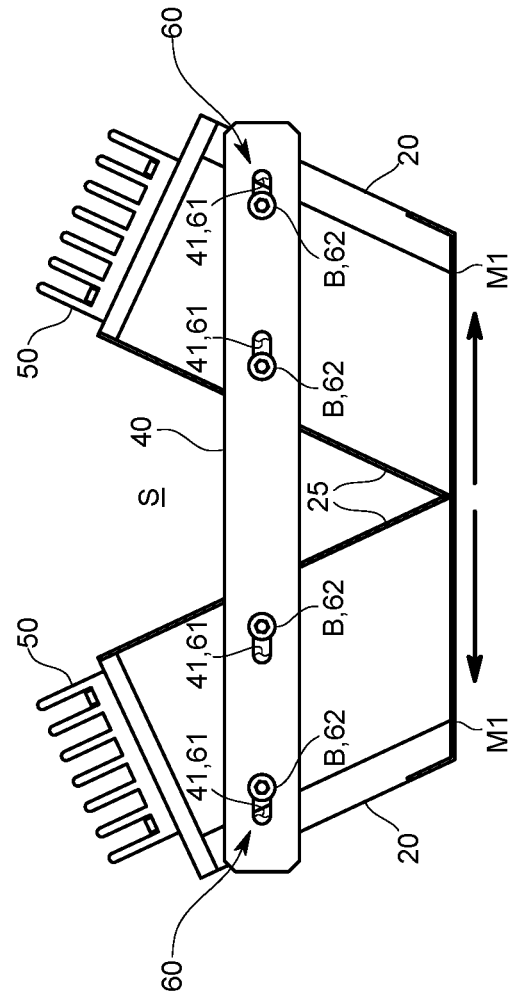

In the present embodiment, the slide grooves 61 are through-holes 41 formed in the connecting members 40, the sliding bodies 62 are fastener B such as bolts, and as illustrated in FIGS. 4A and 4B, by sliding the fasteners B along the through-holes 41, the slit width can be changed within a predetermined range.

According to the light projection device 100 configured as described above, since the slit S allowing the light reflected by the workpiece W to pass from the light emitting surfaces 11 side toward the opposite side has the tapered shape whose width gradually increases from the light emitting surfaces 11 side toward the opposite side, the light emitting surfaces 11 can be suppressed as much as possible from being reduced by the formation of the slit S, and without reducing the amount of light to be projected to the workpiece W, a direction to image the surface of the workpiece W can be changed depending on widening of the slit S.

In doing so, for example, depending on the roughness state of the surface of the workpiece W, the type of a flaw, or the like, by making the imaging device C directly face the workpiece W, an image can be taken with the specular reflection component of the light reflected by the surface of the workpiece W removed, or by tilting the imaging device C, an image can be taken using the specular reflection component. In addition, when the surface of the workpiece W is glossy, making the imaging device C directly face the workpiece W causes the image of the imaging device C itself to be taken, and therefore it is preferable to image the surface of the workpiece W with the imaging device C tilted.

Also, since the light emitting surfaces 11 are flat surfaces, the light emitting surfaces 11 can be brought close to the workpiece W, and light having high illuminance can be projected to the workpiece W.

Further, since the LED boards 31 are tilted such that the slit S sides are farther from the light emitting plate elements 14 than the counter slit sides, and the plurality of LED light sources 32 mounted on the LED boards 31 are arranged on the slit S sides more densely than on the counter slit sides, light from the LED light sources 32 is thoroughly uniformly spread from the slit S sides to counter slit sides of the light emitting plate 10. This makes it possible to, for example, prevent part of the slit S sides of the light emitting plates 11 from darkening as compared with the other parts, and uniform light can be emitted from the light emitting surfaces 11.

Such a working effect is a working effect also producible from the fact that the first reflective plates 241 are larger than the second reflective plates 242.

In addition, since the bottom walls 22 are tilted such that the slit S sides are farther from the light emitting plate elements 14 than the counter slit sides, the heat radiating members 50 provided on the outer surfaces of the bottom walls 22 can be arranged so as to avoid overlap with the slit S, and light passing through the slit S is not blocked by the heat radiating members 50. In doing so, the heat radiating members 50 can be prevented from blocking imaging the workpiece W.

Further in addition, since the pair of light emitting plate elements 14 have the same shape as each other, manufacturing cost can be reduced.

Additionally, since the slit width can be changed by the slit width changing mechanism 60, an imageable area of the surface of the workpiece W can be changed, and inspections can be made corresponding to various flaws and defects.

Note that the present invention is not limited to the above-described embodiment.

Figure 5:
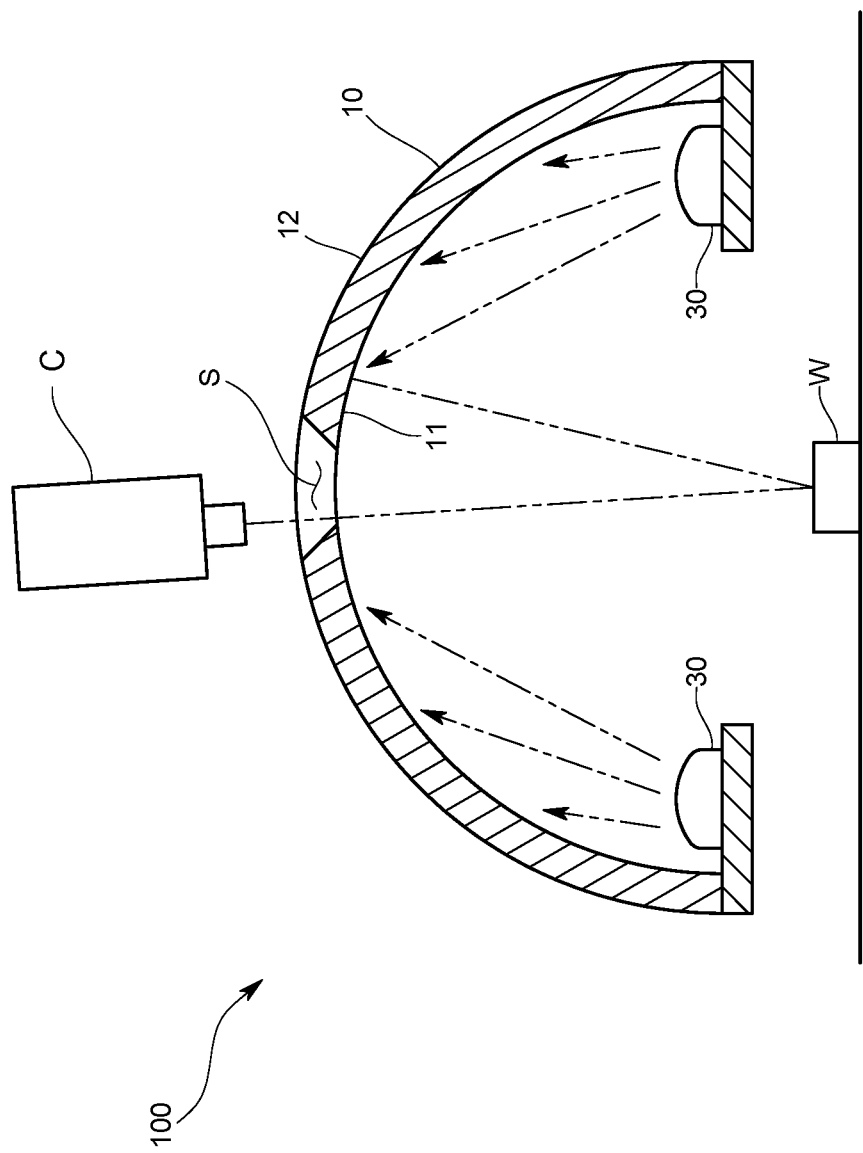
FIG. 5 is an outline view illustrating the configuration of a light projection device in another embodiment.

For example, in the above-described embodiment, the light emitting plate 10 is of a flat plate shape, and the light emitting surfaces 11 thereof are flat surfaces; however, as illustrated in FIG. 5, the light emitting plate 10 may be of, for example, a semicylindrical shape, and the light emitting surfaces 11 may be curved surfaces curved in a direction opposite to the workpiece W as viewed from the extending direction of the slit S.

Also, the slit S in the above-described embodiment is formed by the pair of opposite surfaces 25 of the casings 20; however, as illustrated in FIG. 6, the slit S may be formed penetrating in the central part of one light emitting plate 10 in the thickness direction.

Figure 6A:
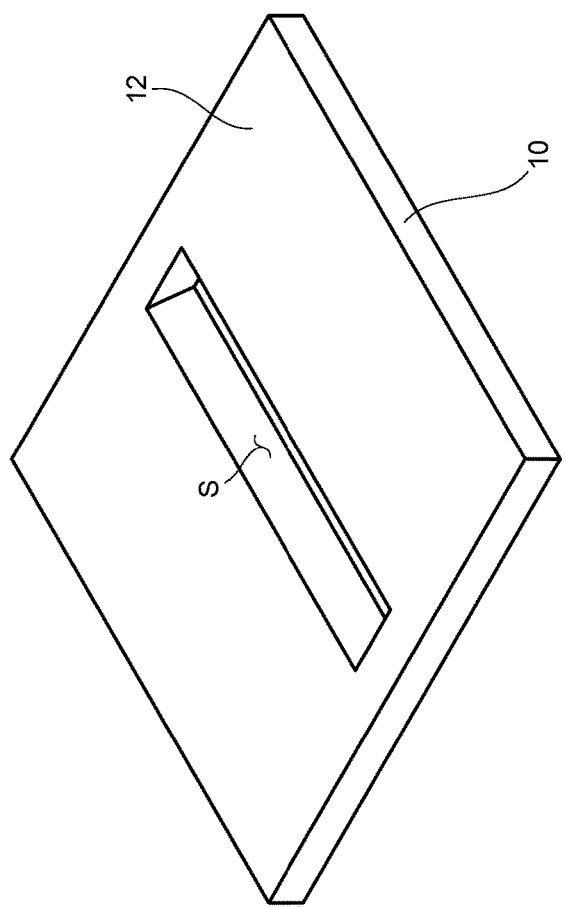
FIGS. 6A and 6B are outline views illustrating a light projection device in still another embodiment.
Figure 6B:
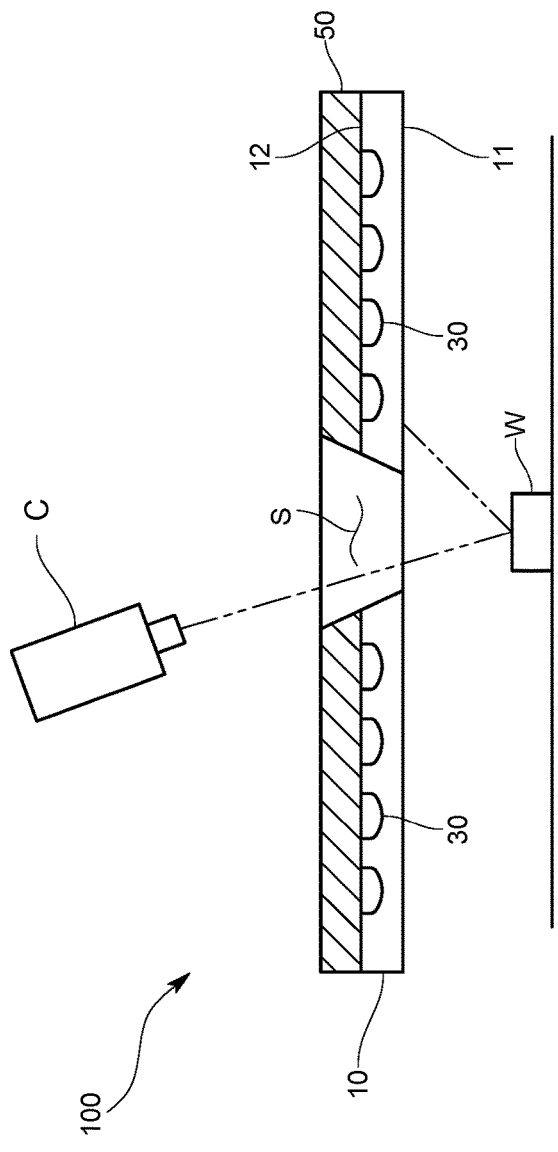

Further, as illustrated in FIGS. 6A and 6B, the light emitting plate 10 may be one having, for example, a substantially square shape in a plan view and a plurality of LED light sources 32 inside. Such a configuration makes it possible to eliminate the need for the casings 20 in the above-described embodiment, and the entire device can be made more compact in the thickness direction.

Note that the shape of the light emitting plate 10 may be variously changed to, for example, a substantially rectangular shape in a plan view, a disc shape in a plan view, or the like.

Figure 7A:
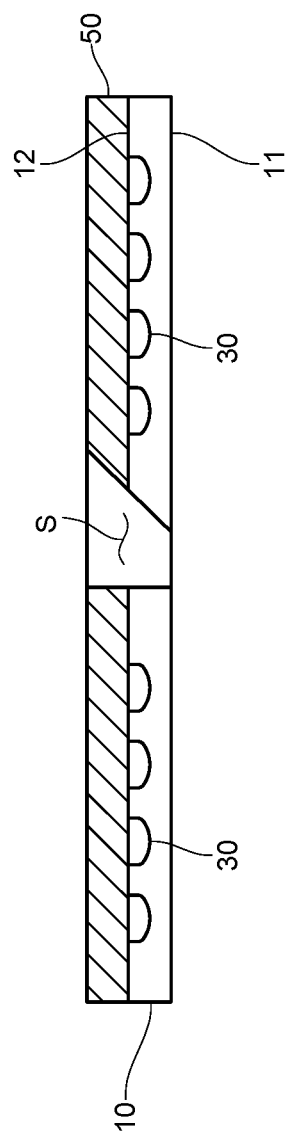
FIGS. 7A and 7B are schematic views illustrating the shapes of a slit in other embodiments.
Figure 7B:
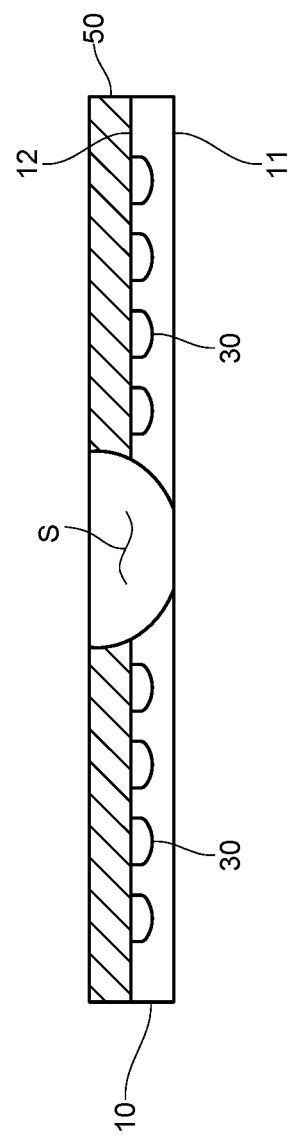

In addition, the slit S may be of, as illustrated in FIG. 7A, a shape that is left-right asymmetric as viewed from the extending direction of the slit S, as illustrated in FIG. 7B, a shape whose width gradually widens while curving from the light emitting surfaces 11 side toward the opposite side, or although not illustrated, a stepwise shape as viewed from the extending direction of the slit S.

Figure 8:
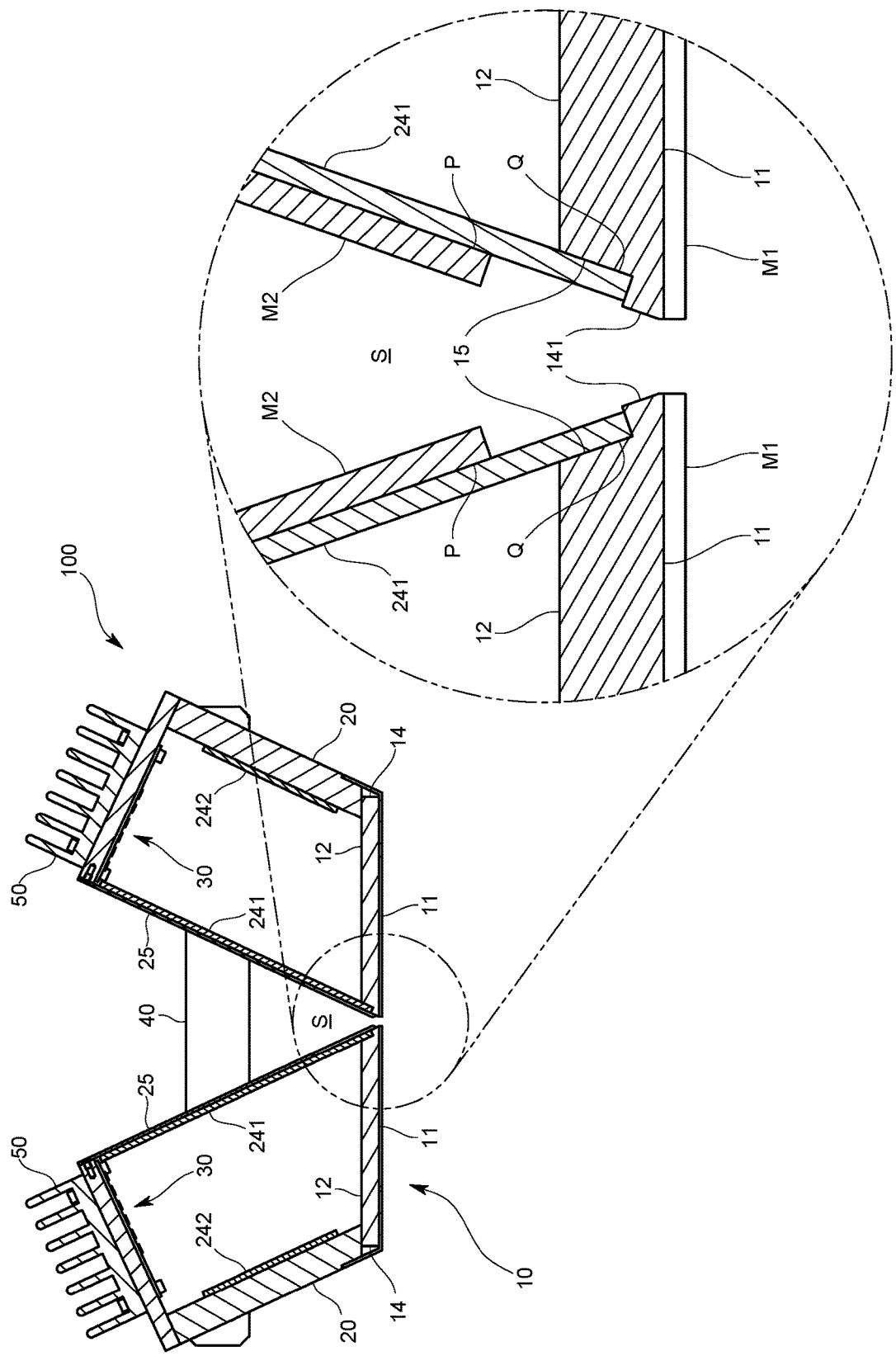
FIG. 8 is a cross-sectional view illustrating the configuration of a light emitting plate in yet another embodiment.

Further in addition, as illustrated in FIG. 8, the respective light emitting plate elements 14 constituting the light emitting plate 10 may be such that the one side surfaces 141 are formed with step parts 15.

Such a configuration makes it possible to fix the first reflective plates 241 by pressing them against the step parts 15 via adhesive members such as double-sided tapes, and the first reflective plates 241 can be easily attached.

Note that in the configuration illustrated in FIG. 8, end parts P of the metal plates M2 on the light emitting surfaces side are farther from the light emitting surfaces 11 than end parts Q of the first reflective plates 241 on the light emitting surfaces side, and the end parts Q of the first reflective plates 241 on the light emitting surfaces side are exposed.

Additionally, the light emitting plate elements 14 in the above-described embodiment are configured such that the one side surfaces 141 are tilted; however, the one side surfaces 141 of the light emitting plate elements 14 do not necessarily have to be tilted particularly when the thickness size of the light emitting plate elements 14 is small, or in other cases.

In addition, the present invention is not limited to the above-described embodiments but can be variously modified without departing from the scope thereof.

INDUSTRIAL APPLICABILITY

According to the present invention configured as described, the surface of a workpiece can be imaged from a plurality of directions without reducing the amount of light to be projected to the workpiece.

The invention claimed is:
1. A light projection device comprising:
a pair of light emitting surfaces facing a workpiece and formed with a slit allowing light reflected by the workpiece to pass from a light emitting surface side of a pair of light emitting plates to an opposite side thereof, each light emitting plate formed with one of the pair of light emitting surfaces so as to form the pair of light emitting surfaces; and
a pair of casings with a pair of side surfaces facing opposite to each other and a pair of openings closed by the pair of light emitting plates, each casing containing a plurality of LED light sources, wherein
the pair of side surfaces of the pair of casings are arranged such that a width between the pair of side surfaces gradually increases from the light emitting surface side toward the opposite side along an entire length of the side surfaces, and
the pair of side surfaces of the pair of casings form the slit having a shape whose width gradually increases from the light emitting surface side toward the opposite side.
2. The light projection device according to claim 1, wherein
each of the light emitting surfaces is a flat surface.
3. The light projection device according to claim 2, wherein
the plurality of LED light sources are provided on a side opposite to the workpiece with respect to the light emitting surfaces.
4. A light projection device comprising:
a pair of light emitting surfaces facing a workpiece and formed with a slit allowing light reflected by the workpiece to pass from a light emitting surface side of a pair of light emitting plates to an opposite side thereof, each light emitting plate formed with one of the pair of light emitting surfaces so as to form the pair of light emitting surfaces; and a pair of casings with a pair of side surfaces facing opposite to each other and a pair of openings closed by the pair of light emitting plates, each casing containing a plurality of LED light sources, wherein the slit is formed by at least one of:
the pair of side surfaces of the pair of casings; and
the pair of light emitting plates, the slit has a shape whose width gradually increases from the light emitting surface side toward the opposite side, the openings are of a substantially rectangular shape, among side walls of the casings, the side walls forming the openings, inner surfaces of side walls on slit sides and inner surfaces of side walls on counter slit sides are provided with reflective members adapted to reflect light from the LED light sources toward the openings, and reflective members on the slit sides are larger in area of a reflective surface than reflective members on the counter slit sides.

5. The light projection device according to claim 1, further comprising:
a connecting member connecting the pair of casings, wherein
the connecting member includes a slit width changing mechanism adapted to change a separation distance between the pair of casings and change the width of the slit.

6. The light projection device according to claim 3, wherein
the plurality of LED light sources are provided sandwiching the slit on both sides thereof, and arranged more densely toward the slit sides than toward the counter slit sides.

7. A light projection device comprising:
a pair of light emitting surfaces facing a workpiece and formed with a slit allowing light reflected by the workpiece to pass from a light emitting surface side of a pair of light emitting plates to an opposite side thereof, each light emitting plate formed with one of the pair of light emitting surfaces so as to form the pair of light emitting surfaces;

a pair of casings with a pair of side surfaces facing opposite to each other and a pair of openings closed by the pair of light emitting plates, each casing containing a plurality of LED light sources; and LED boards that are provided sandwiching the slit, on both sides thereof, and opposite to the light emitting plate, and mounted with the plurality of LED light sources, wherein the slit is formed by at least one of:
the pair of side surfaces of the pair of casings; and
the pair of light emitting plates, the slit has a shape whose width gradually increases from the light emitting surface side toward the opposite side, and the LED boards are arranged tilted such that the LED boards on slit sides are farther from the light emitting plate than the LED boards on counter slit sides.

8. The light projection device according to claim 7, wherein
bottom walls of the casings are tilted such that the slit sides are farther from the light emitting plate than the counter slit sides, the bottom walls being opposite to the light emitting plate, and inner surfaces of the bottom walls are provided with the LED boards, and outer surfaces of the bottom walls are provided with heat radiating members.

* * * * *